US011683107B2

(12) United States Patent
Wright et al.

(10) Patent No.: US 11,683,107 B2
(45) Date of Patent: Jun. 20, 2023

(54) AUTHENTICATION BY DIELECTRIC PROPERTIES OF SKIN

(71) Applicant: Nokia Technologies Oy, Espoo (FI)

(72) Inventors: Christopher Wright, London (GB); Phil Catton, Cambridge (GB); Wai Lau, London (GB)

(73) Assignee: Nokia Technologies Oy, Espoo (FI)

( * ) Notice: Subject to any disclaimer, the term of this patent is extended or adjusted under 35 U.S.C. 154(b) by 114 days.

(21) Appl. No.: 17/474,458

(22) Filed: Sep. 14, 2021

(65) Prior Publication Data

US 2022/0094456 A1 Mar. 24, 2022

(30) Foreign Application Priority Data

Sep. 23, 2020 (EP) ................................ 20197638

(51) Int. Cl.
| H04B 17/391 | (2015.01) |
| G01N 27/02 | (2006.01) |
| H04B 13/00 | (2006.01) |

(52) U.S. Cl.
CPC .......... *H04B 17/391* (2015.01); *G01N 27/02* (2013.01); *H04B 13/005* (2013.01)

(58) Field of Classification Search
CPC ..... H04B 17/391; H04B 13/005; G01N 27/02
See application file for complete search history.

(56) References Cited

U.S. PATENT DOCUMENTS

| 9,743,364 | B2 | 8/2017 | Mng et al. | |
| 2011/0137133 | A1* | 6/2011 | Espina Perez | G16H 40/67 |
| | | | | 600/300 |
| 2013/0064311 | A1* | 3/2013 | Turner | H04B 5/02 |
| | | | | 375/259 |
| 2016/0294486 | A1* | 10/2016 | Bolin | H04L 5/0048 |
| 2019/0011534 | A1 | 1/2019 | Trotta et al. | |
| 2020/0203812 | A1* | 6/2020 | Murray | H01Q 9/285 |

OTHER PUBLICATIONS

Korphi et al., "mmWave Radar Return for Characterization of Burned Skin", Technical Disclosure Commons, Oct. 17, 2019, pp. 1-12.
Owda et al., "The Reflectance of Human Skin in the Millimeter-Wave Band", Sensors, vol. 20, 2020, pp. 1-22.

(Continued)

*Primary Examiner* — Brenda H Pham
(74) *Attorney, Agent, or Firm* — Nokia Technologies Oy (57) ABSTRACT

According to various, but not necessarily all, embodiments there is provided an apparatus comprising means for: obtaining a propagation profile for wireless signals transmitted between at least two devices via a creeping wave along a user's skin; causing transmission of electromagnetic radiation towards a plurality of locations on a target user's body to obtain dielectric properties of their skin at the plurality of locations based on an amount of the electromagnetic radiation reflected from each location; determining whether the propagation profile correlates with a realizable creeping wave along the target user's skin, the realizability being based on the obtained dielectric properties of their skin; and forming an association between the target user and the at least two devices based on a strength of correlation between the propagation profile and a realizable creeping wave.

20 Claims, 3 Drawing Sheets

(56) References Cited

OTHER PUBLICATIONS

Zhang et al., "On-body skin confined propagation for Body Area Networks (BAN)", 11th European Conference on Antennas and Propagation (EUCAP), Mar. 2017, 3 pages.

Wang et al., "Securing On-Body IoT Devices by Exploiting Creeping Wave Propagation", arXiv, Jan. 28, 2018, pp. 1-13.

Zhao et al., "Authentication in Millimeter-wave Body-centric Networks Through Wireless Channel Characterization", IEEE Transactions on Antennas and Propagation, vol. 65, No. 12, Mar. 2017, pp. 1-8.

Wang et al., "Detecting On-body Devices Through Creeping Wave Propagation", IEEE Conference on Computer Communications, May 1-4, 2017, 9 pages.

Gu et al., "Mmsense: Multi-person Detection and Identification via Mmwave Sensing", Proceedings of the 3rd ACM Workshop on Millimeter-wave Networks and Sensing Systems, Oct. 2019, pp. 45-50.

Umar et al., "Mutual Authentication in Body Area Networks Using Signal Propagation Characteristics", IEEE Access, vol. 8, Apr. 2, 2020, pp. 66411-66422.

Mortazavi et al., "Can Smartwatches Replace Smartphones for Posture Tracking?", Sensors, vol. 15, No. 10, Oct. 2015, pp. 26783-26800.

Sengupta et al., "mm-Pose: Real-Time Human Skeletal Posture Estimation using mmWave Radars and CNNs", arXiv, Nov. 21, 2019, pp. 1-12.

Extended European Search Report received for corresponding European Patent Application No. 20197638.8, dated Mar. 15, 2021, 11 pages.

Hwang et al., "110 GHz broadband measurement of permittivity on human epidermis using 1 mm coaxial probe", IEEE MTT-S International Microwave Symposium Digest, Jun. 8-13, 2003, pp. 399-402.

Stuchly et al., "Coaxial Line Reflection Methods for Measuring Dielectric Properties of Biological Substances at Radio and Microwave Frequencies—A Review", IEEE Transactions on Instrumentation and Measurement, vol. 29, No. 3, Sep. 1980, pp. 176-183.

Khan et al., "Recent Advancements in User Effect Mitigation for Mobile Terminal Antennas: A Review", IEEE Transactions on Electromagnetic Compatibility, vol. 61, No. 1, Feb. 2019, pp. 279-287.

Wu et al., "Safe for Generations to Come: Considerations of Safety for Millimeter Waves in Wireless Communications", IEEE Microwave Magazine, vol. 16, No. 2, Mar. 2015, pp. 65-84.

* cited by examiner

AUTHENTICATION BY DIELECTRIC PROPERTIES OF SKIN

RELATED APPLICATION

This application claims priority to the European patent application number 20197638.8, filed on Sep. 23, 2020, the content of which is hereby incorporated in their entirety.

TECHNOLOGICAL FIELD

Embodiments of the present disclosure relate to authentication by dielectric properties of skin. Some embodiments relate to authentication of users or devices using dielectric properties of skin.

BACKGROUND

The propagation characteristics of wireless signals exchanged between devices located within, on, or in the immediate proximity of a human body differ from those propagating over off-body links. Devices in Body Area Networks can therefore be authenticated by considering the propagation characteristics of incoming wireless signals.

BRIEF SUMMARY

According to various, but not necessarily all, embodiments there is provided an apparatus comprising means for: obtaining a propagation profile for wireless signals transmitted between at least two devices via a creeping wave along a user's skin; causing transmission of electromagnetic radiation towards a plurality of locations on a target user's body to obtain dielectric properties of their skin at the plurality of locations based on an amount of the electromagnetic radiation reflected from each location; determining whether the propagation profile correlates with a realizable creeping wave along the target user's skin, the realizability being based on the obtained dielectric properties of their skin; and forming an association between the target user and the at least two devices based on a strength of correlation between the propagation profile and a realizable creeping wave.

According to various, but not necessarily all, embodiments there is provided a method comprising: obtaining a propagation profile for wireless signals transmitted between at least two devices via a creeping wave along a user's skin; causing transmission of electromagnetic radiation towards a plurality of locations on a target user's body to obtain dielectric properties of their skin at the plurality of locations based on an amount of the electromagnetic radiation reflected from each location; determining whether the propagation profile correlates with a realizable creeping wave along the target user's skin, the realizability being based on the obtained dielectric properties of their skin; and forming an association between the target user and the at least two devices based on a strength of correlation between the propagation profile and a realizable creeping wave.

According to various, but not necessarily all, embodiments there is provided a computer program that, when run on a computer, performs: obtaining a propagation profile for wireless signals transmitted between at least two devices via a creeping wave along a user's skin; causing transmission of electromagnetic radiation towards a plurality of locations on a target user's body to obtain dielectric properties of their skin at the plurality of locations based on an amount of the electromagnetic radiation reflected from each location; determining whether the propagation profile correlates with a realizable creeping wave along the target user's skin, the realizability being based on the obtained dielectric properties of their skin; and forming an association between the target user and the at least two devices based on a strength of correlation between the propagation profile and a realizable creeping wave.

According to various, but not necessarily all, embodiments there is provided examples as claimed in the appended claims.

The scope of protection sought for various embodiments of the invention is set out by the independent claims. The embodiments and features, if any, described in this specification that do not fall under the scope of the independent claims are to be interpreted as examples useful for understanding various embodiments of the invention.

The following portion of this "Brief Summary" section, describes various features that may be features of any of the embodiments described in the foregoing portion of the 'Brief Summary' section. The description of a function should additionally be considered to also disclose any means suitable for performing that function.

The propagation profile may indicate attenuation of one or more frequencies of the wireless signals.

The propagation profile may be received from one of the at least two devices.

The apparatus may be, or may be comprised in, one of the at least two devices and may obtain the propagation profile by analysis of wireless signals received from another of the at least two devices.

The propagation profile may be contemporaneously obtained along with the dielectric properties of the target user's skin based on reflections of the electromagnetic radiation.

The propagation profile may be retrieved from storage.

The at least two devices may be Wireless Body Area Network (WBAN) devices.

The apparatus may be, or may be comprised in, a WBAN device.

The electromagnetic radiation transmitted towards the plurality of locations may comprise at least one radiofrequency beam having a wavelength below approximately 10 mm.

The transmission of electromagnetic radiation towards the plurality of locations on the target user's body may be caused in response to a trigger event.

The plurality of locations towards which the electromagnetic radiation is transmitted may comprise expected locations on the target user's body of the at least two devices.

The plurality of locations may comprise locations along an approximate geodesic path between expected locations of the at least two devices.

Electromagnetic radiation reflected from the plurality of locations may be received and the dielectric properties of the target user's skin at the plurality of locations obtained based on an amount of the electromagnetic radiation reflected from each location The dielectric properties of the target user's skin at the plurality of locations may be obtained based on the amount of the electromagnetic radiation reflected back to the apparatus.

Propagation profiles for realizable creeping waves my be predicted based on obtained dielectric properties of the target user's skin.

The propagation profiles may be predicted for realizable creeping waves between expected locations on the target user's body of the at least two devices.

Dielectric properties of the target user's skin may be predicted based on the obtained propagation profile.

Information about the target user's body's pose may be obtained.

The realizability may be further based on obtained information about the target user's body's pose.

Locations of the at least two devices on the target user's body may be determined from a path of a realizable creeping wave which correlates with the obtained propagation profile.

The locations of the at least two devices on the target user's body may be used to assess, based on a directionality of incoming wireless signals, whether the incoming wireless signals are transmitted from one of the at least two devices.

Connection of the apparatus with the at least two devices may be approved if there is an association between the target user and at least two devices and if the target user is an authorized user of the apparatus.

Access for the target user to applications run on the apparatus may be approved if there is an association between the target user and the at least two devices and if the at least two devices are approved to connect with the apparatus.

BRIEF DESCRIPTION

Some examples will now be described with reference to the accompanying drawings in which.

DETAILED DESCRIPTION

The dielectric properties of skin (for example, human skin) are strongly correlated with skin thickness and moisture content. Skin thickness and moisture content vary between individuals. Skin thickness and moisture content also vary with locations over an individual's body. Accordingly, a map of dielectric properties of the skin to locations on an individual's body will be unique to that individual.

Figure 1A:
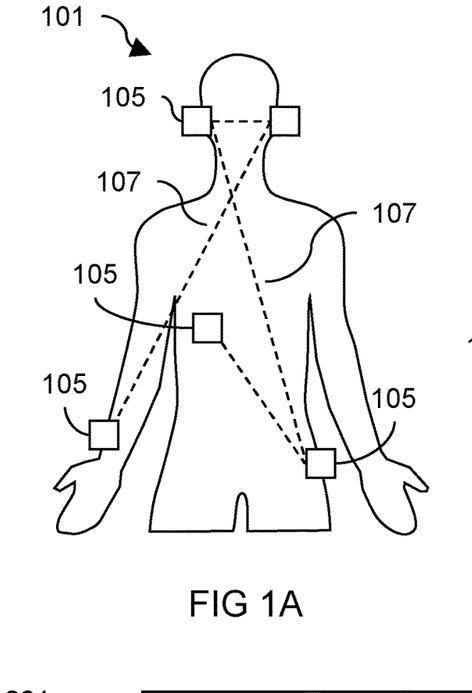
FIGS. 1A and 1B show examples of the disclosure.
Figure 1B:
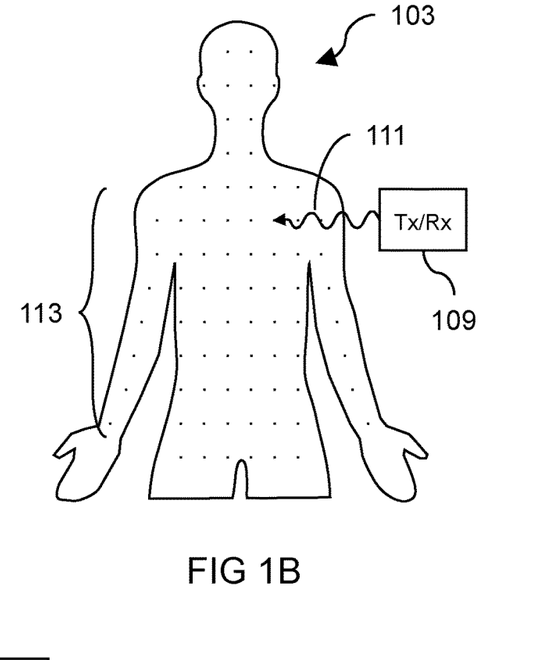

FIGS. 1A and 1B show examples of measuring dielectric properties of skin.

In FIG. 1A dielectric properties of the skin of a user 101 can be obtained from wireless signals 107 between at least two devices 105 communicating with each other via creeping waves along the user's skin. Creeping waves can propagate along dielectric-air interfaces by means of diffraction. Hence, the wireless signals 107 exchanged between the at least two devices 105 are diffracted around the body along the body's surface (skin). The wireless signals 107 can, by means of this diffraction, propagate between at least two devices 105 which are not within one another's line-of-sight. The profile of the propagation of creeping waves is dependent on the dielectric properties of the dielectric in the dielectric-air interface. Different dielectric properties result in different path loss or attenuation. Accordingly, the propagation of the wireless signals 107 is dependent on the dielectric properties of the user's skin.

The at least two devices 105 may be Wireless Body Area Network (WBAN) devices. The WBAN is a computer network which interconnects electronic devices 105 via wireless signals within, on, and in the immediate proximity of the user's body. The propagation of these wireless signals is dominated by creeping waves. The at least two devices 105 are electronic devices within, on, or in the immediate proximity of the user's body. For example, the at least two devices 105 can comprise: electronic devices embedded in the user's body as implants; wearable electronic devices; and/or accompanied electronic devices which can be carry by the user 105 in different positions about their person, such as in pockets of their clothes, in their bags, or in their hands.

In FIG. 1B dielectric properties of the skin of a target user 103 are measured using electromagnetic radiation 111 reflected from their skin. A transceiver 109 transmits electromagnetic radiation 111 towards a plurality of different locations 113 on the target user's body and receives the electromagnetic radiation 111 reflected from the plurality of locations 113. The amount of reflected radiation 111 which is received depends on the dielectric properties of the skin.

The transceiver 109 can comprise any means that can be configured to enable the electromagnetic radiation 111 to be transmitted and received. The transceiver 109 can be configured to enable beam forming so that one or more beams of the electromagnetic radiation 111 can be provided by the transceiver 109. The transceiver 109 can comprise a plurality of antenna elements to enable the beams to be provided. The transceiver 109 can be configured to enable sweeping of the beam of the electromagnetic radiation 111. That is, the transceiver 109 can be configured to enable the beam to be directed in a plurality of different angles and thus towards the plurality of locations 113 on the target user's body. In some examples the beams of the electromagnetic radiation 111 can be directed in a plurality of different angles at the same time. For instance, digital beamforming can enable a plurality of different beams of the electromagnetic radiation 111 to be provided in different directions at the same time. In other examples the beams can be directed in different directions at different times. Accordingly, the electromagnetic radiation 111 can be transmitted towards the plurality of different locations 113 on the target user's body contemporaneously or sequentially.

The electromagnetic radiation 111 transmitted towards the plurality of locations 113 may comprises at least one radiofrequency beam. In some examples the radiofrequency beam has a wavelength below approximately 10 mm. The radiofrequency beam may be in the millimetre-wave (mmWave) band, having wavelengths from approximately 10 to 1 mm. mmWave is used for 5G communication. mmWave is used for communication within New Radio networks. New Radio is the 3GPP (3rd Generation Partnership Project) name for 5G technology. Thus, the transceiver 109 can be configured to enable 5G communication.

The electromagnetic radiation 111 can alternatively comprise microwave or near-infrared frequencies.

Dielectric properties comprise permittivity at one or more frequencies. The permittivity is a complex relative permittivity for which the real part is the dielectric constant representing an amount of energy from an electric field arising from, for example, the wireless signals 107 or the transmitted electromagnetic radiation 111, that is stored in the skin and the imaginary part is the dissipation or loss factor representing the amount of energy loss from the skin due to the electric field.

By comparing dielectric properties of skin measured in the manner of FIG. 1A with those measured in the manner of FIG. 1B, it can be determined whether the user 101 is the same person as the target user 103. Thus, authentication based on dielectric properties of skin can be realized. Examples of the present disclosure utilize authentication based on dielectric properties of skin.

Figure 2:
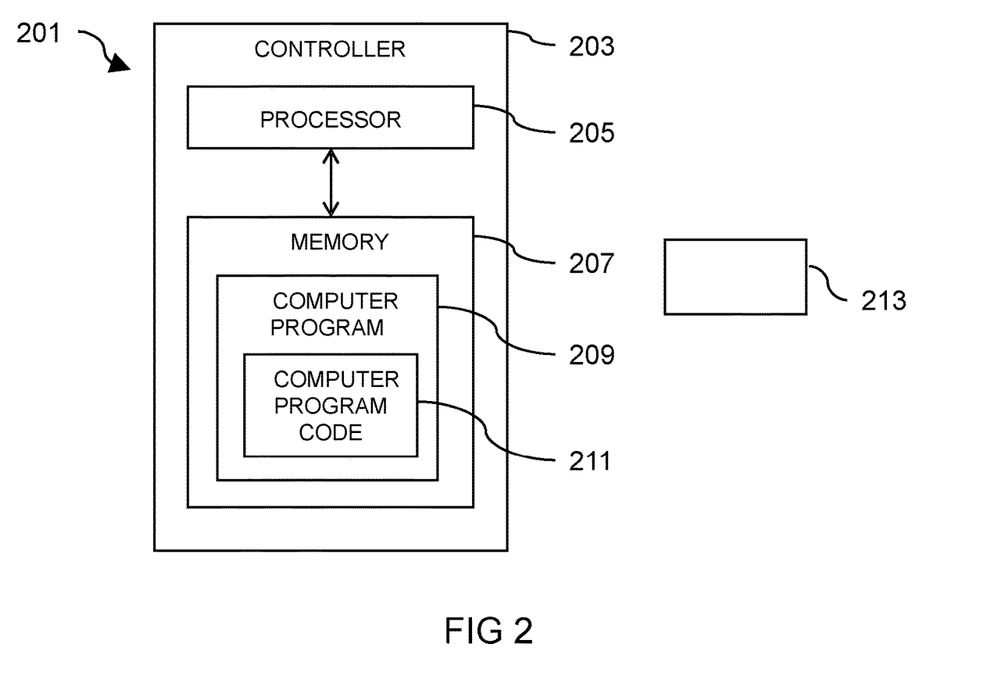
FIG. 2 shows an example apparatus.

FIG. 2 schematically illustrates an apparatus 201 according to examples of the disclosure. The apparatus 201 illustrated in FIG. 2 may be a chip or a chip-set. In some examples the apparatus 201 may be or be comprised within a user device, such as a mobile phone or another portable computing device, comprising a transceiver 109, as described in relation to FIG. 1B, for transmitting and receiving the electromagnetic radiation 111. The user device may be a WBAN device and may be one of the at least two devices 105.

In the example of FIG. 2 the apparatus 201 comprises a controller 203. Implementation of the controller 203 may be as controller circuitry. The controller 203 may be implemented in hardware alone, have certain aspects in software including firmware alone or can be a combination of hardware and software (including firmware).

As illustrated in FIG. 2 the controller 203 may be implemented using instructions that enable hardware functionality, for example, by using executable instructions of a computer program 209 in a general-purpose or special-purpose processor 205 that may be stored on a computer readable storage medium (disk, memory, etc.) to be executed by such a processor 205.

The processor 205 is configured to read from and write to the memory 207. The processor 205 may also comprise an output interface via which data and/or commands are output by the processor 205 and an input interface via which data and/or commands are input to the processor 205.

The memory 207 stores a computer program 209 comprising computer program instructions (computer program code 211) that controls the operation of the apparatus 201 when loaded into the processor 205. The computer program instructions, of the computer program 209, provide the logic and routines that enables the apparatus 201 to perform the method 301 illustrated in FIG. 3 and optionally the methods illustrated in FIGS. 4 and 5. The processor 205 by reading the memory 207 is able to load and execute the computer program 209.

Figure 3:
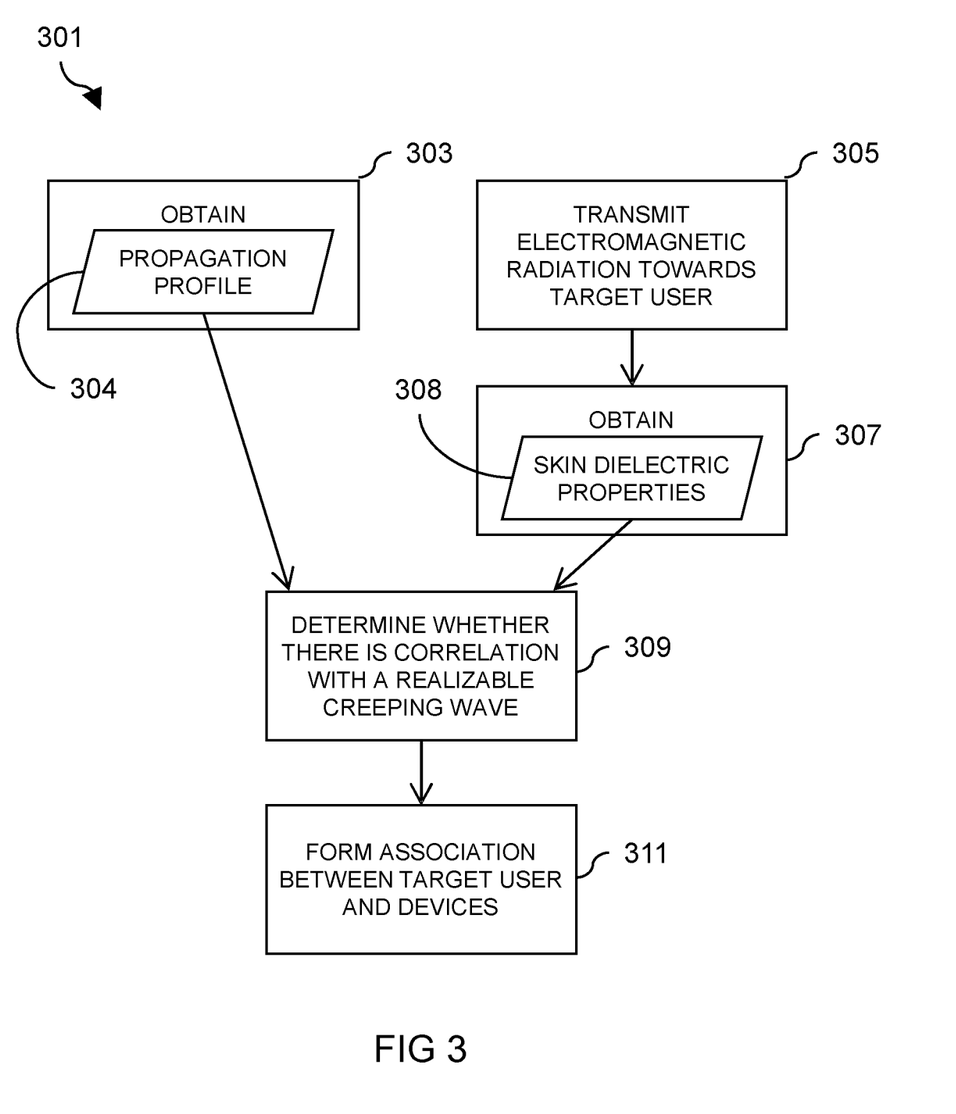
FIG. 3 shows an example method.

The apparatus 201 therefore comprises: at least one processor 205; and at least one memory 207 including computer program code 211, the at least one memory 207 and the computer program code configured to, with the at least one processor 205, cause the apparatus 201 at least to perform: obtaining 303 a propagation profile 304 for wireless signals 107 transmitted between at least two devices 105 via a creeping wave along a user's skin; causing transmission 305 of electromagnetic radiation 111 towards a plurality of locations 113 on a target user's body to obtain 307 dielectric properties 308 of their skin at the plurality of locations 113 based on an amount of the electromagnetic radiation 111 reflected from each location 113; determining 307 whether the propagation profile 304 correlates with a realizable creeping wave along the target user's skin, the realizability being based on the obtained dielectric properties 308 of their skin; and forming 309 an association between the target user 103 and the at least two devices 105 based on a strength of correlation between the propagation profile 304 and a realizable creeping wave.

As illustrated in FIG. 2, the computer program 209 may arrive at the apparatus 201 via any suitable delivery mechanism 213. The delivery mechanism 213 may be, for example, a machine readable medium, a computer-readable medium, a non-transitory computer-readable storage medium, a computer program product, a memory device, a record medium such as a Compact Disc Read-Only Memory (CD-ROM) or a Digital Versatile Disc (DVD) or a solid state memory, an article of manufacture that comprises or tangibly embodies the computer program 209. The delivery mechanism may be a signal configured to reliably transfer the computer program 209. The apparatus 201 may propagate or transmit the computer program 209 as a computer data signal. In some examples the computer program 209 may be transmitted to the apparatus 201 using a wireless protocol such as Bluetooth, Bluetooth Low Energy, Bluetooth Smart, 6LoWPan (IPv6 over low power personal area networks) ZigBee, ANT+, near field communication (NFC), Radio frequency identification, wireless local area network (wireless LAN) or any other suitable protocol.

In some examples there is provided computer program instructions for causing an apparatus 201 to perform at least the following: obtaining 303 a propagation profile 304 for wireless signals 107 transmitted between at least two devices 105 via a creeping wave along a user's skin; causing transmission 305 of electromagnetic radiation 111 towards a plurality of locations 113 on a target user's body to obtain 307 dielectric properties 308 of their skin at the plurality of locations 113 based on an amount of the electromagnetic radiation 111 reflected from each location 113; determining 307 whether the propagation profile 304 correlates with a realizable creeping wave along the target user's skin, the realizability being based on the obtained dielectric properties 308 of their skin; and forming 309 an association between the target user 103 and the at least two devices 105 based on a strength of correlation between the propagation profile 304 and a realizable creeping wave.

The computer program instructions may be comprised in a computer program 209, a non-transitory computer readable medium, a computer program product, a machine readable medium. In some but not necessarily all examples, the computer program instructions may be distributed over more than one computer program 209.

Although the memory 207 is illustrated as a single component/circuitry it may be implemented as one or more separate components/circuitry some or all of which may be integrated/removable and/or may provide permanent/semi-permanent/dynamic/cached storage.

Although the processor 205 is illustrated as a single component/circuitry it may be implemented as one or more separate components/circuitry some or all of which may be integrated/removable. The processor 205 may be a single core or multi-core processor.

References to "computer-readable storage medium", "computer program product", "tangibly embodied computer program" etc. or a "controller", "computer", "processor" etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" may refer to one or more or all of the following:
(a) hardware-only circuitry implementations (such as implementations in only analog and/or digital circuitry) and
(b) combinations of hardware circuits and software, such as (as applicable):
(i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions and (c) hardware circuit(s) and or processor(s), such as a microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor and its (or their) accompanying software and/or firmware. The term circuitry also covers, for example and if applicable to the particular claim element, a baseband integrated circuit for a mobile device or a similar integrated circuit in a server, a cellular network device, or other computing or network device.

Figure 4:
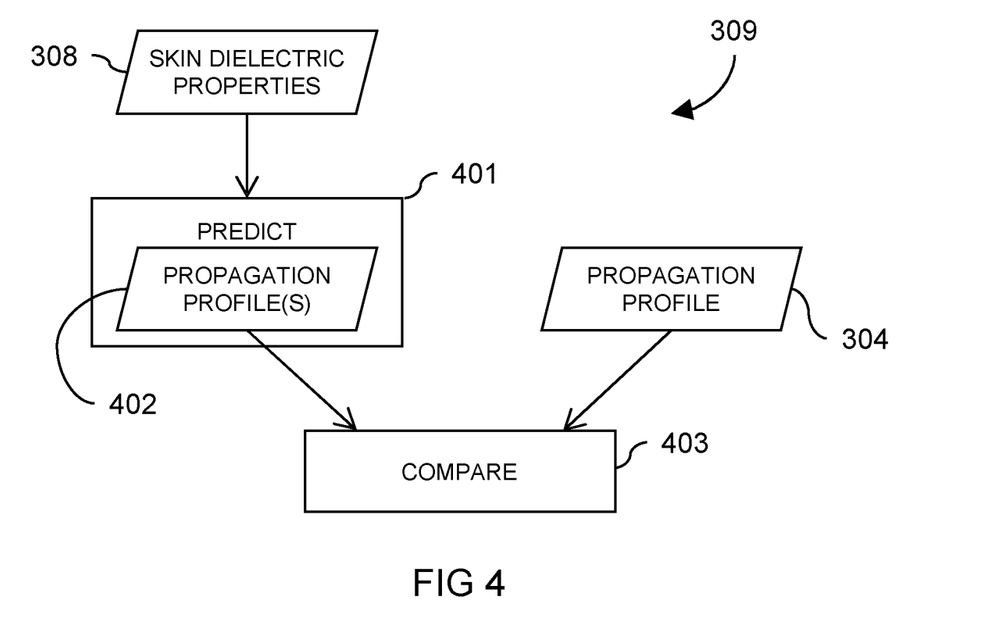
FIG. 4 shows an example method.
Figure 5:
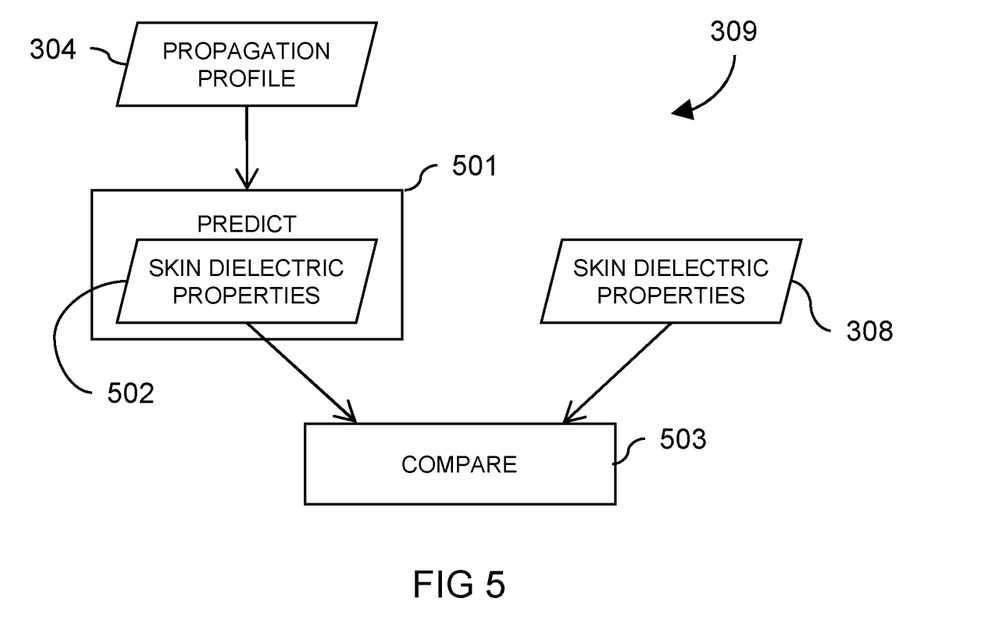
FIG. 5 shows an example method.

The blocks illustrated in FIG. 3 and optionally those illustrated in FIGS. 4 and 5 may represent steps in a method and/or sections of code in the computer program 209. The illustration of a particular order to the blocks does not necessarily imply that there is a required or preferred order for the blocks and the order and arrangement of the blocks may be varied. Furthermore, it may be possible for some blocks to be omitted.

FIG. 3 shows an example method 301 that can be implemented by the apparatus 201 as shown in FIG. 2.

The method 301 comprises, at block 303, obtaining a propagation profile 304 for wireless signals 107 transmitted between at least two devices 105 via a creeping wave along the skin of the user 101. The propagation profile can indicate attenuation of one or more frequencies of the wireless signals 107. The wireless signals 107 exchanged between the at least two devices 105 may be of a known waveform so that the propagation profile 303 can be obtained by comparison of a received wireless signal 107 with that which would have been transmitted.

In some examples the propagation profile 304 is obtained by the apparatus 201 receiving this data from one of the at least two devices 205. That is, the wireless signals 107 passed between the devices 105 are analyzed by at least one of the devices 105 to determine the propagation profile 304. The propagation profile 304 is subsequently transmitted to the apparatus 201.

The propagation profile 304 can be determined by the analysis of wireless signals 107 which propagate between the at least two devices 105 during, or closely before or after, the transmission of electromagnetic radiation 111 towards the target user 103 to obtain dielectric properties 308 of their skin as described below with reference to block 305 of the method 301. Accordingly, the method 301 is not affected by variations in dielectric properties over time, such as could be caused by changes in hydration, though such effects may be systematic and therefore accounted for if the wireless signals 107 from which the propagation profile 304 is obtained are not those which are exchanged between the at least two devices 105 contemporaneously with the transmission of the electromagnetic radiation 111.

In other examples the apparatus 201 is or is comprised in one of the at least two devices 105 and obtains the propagation profile 304 by analysis of wireless signals received from another of the at least two devices 105. For example, the apparatus 201 can be a WBAN device and communicate with at least one other device 105 by wireless signals propagating therebetween as creeping waves. The apparatus 201 can be positioned on or in the immediate proximity of the body of the user 101 prior to performance of the method 301 or at least prior to the performance of blocks 305, 307, 309, and 311 of the method 301.

The propagation profile 304 obtained by the apparatus 201, either through analysis of received wireless signals 107 from others of the at least two devices 105 or as received from one of the at least two devices 105, can be recorded in the form of an addressable data structure that is retrievable from an addressable memory space (for example, the memory 207) and can therefore be stored and retrieved until deleted or over-written, although long-term storage may or may not occur. In block 303, to obtain the propagation profile 304, it may be retrieved from storage.

The frequency of the wireless signals 107 can be varied. Frequency determines the penetration depth. Higher frequencies will produce a skin property dependence in the more surface layers. For example, at 60 GHz, the penetration depth will be about 0.5 mm. Therefore, varying the frequency of the wireless signals 107 enables propagation profiles 304 to be obtained for different depths of the skin.

At block 305 of the method 301 electromagnetic radiation 111 is caused to be transmitted towards a plurality of locations 113 on the body of the target user 103 and at block 307 of the method 301 dielectric properties 308 of their skin at the plurality of locations 113 are obtained based on an amount of the electromagnetic radiation 111 reflected from each location 113.

In some examples the plurality of locations 113 may be correlated with on-body locations by obtaining body geometry information from, for example, measurements made with visual or time-of-flight sensors. Measurements of the manner in which the target user 103 grips the apparatus 201, or a device in which it is comprised, and of the orientation of the apparatus 201 can also be used to estimate head and body positions.

Where the electromagnetic radiation 111 is transmitted from the apparatus 201, the dielectric properties 308 of the skin of the target user 103 can be obtained based on the amount of the electromagnetic radiation 111 reflected back to the apparatus 201, where it may be received, transduced into an electrical signal and processed.

The processing may comprise deconvolving the component of the reflected electromagnetic radiation 111 which is due to the dielectric properties 308 to separate it from the component due to the angle of incidence the transmitted electromagnetic radiation 111 makes with the skin and the surface roughness of the skin. In examples such as those where the electromagnetic radiation 111 is in the mmWave band, the surface roughness of skin may considerably less than the wavelength of radiation and thus the skin can be treated as a specular reflector. The angle of the skin relative to the transceiver 109, and thus the angle of incidence, can be estimated by, for example, time-of-flight measurements, or by image analysis, or based on a current pose of the target user 103.

The component of the reflected electromagnetic radiation 111 which is due to the dielectric properties 308 can be input to a machine-learned algorithm which has been trained to map an amount of reflected electromagnetic radiation 111 to dielectric properties 308 using a training set comprising, for example, ground truth amounts of reflected radiation from materials of known dielectric properties. In some examples, rather than deconvolving the component of the reflected electromagnetic radiation 111 which is due to the dielectric properties 308, the received amount of electromagnetic radiation 111 reflected back to the apparatus 201 can be input into a machine-learned model along with angle of incidence and, optionally, surface roughness, the machine-learned algorithm being trained to map these input variables to dielectric properties 308.

Alternatively, the component of the reflected electromagnetic radiation 111 which is due to the dielectric properties 308 can be processed using a specified model (set of rules). In some examples the specified model may relate the normal and parallel polarization reflectivities of skin $\Gamma_n$, $\delta_P$ with the permittivity of skin $\varepsilon_{skin}$, the permittivity of air $\varepsilon_{air}$, and the angles of incidence and transmission $\theta_i$, $\theta_t$. The polarization reflectivities $\delta_n$, $\delta_P$ can be obtained from the component of the reflected electromagnetic radiation 111 which is due to the dielectric properties 308. The permittivity of air $\varepsilon_{air}$ is known. If the skin is assumed to be a specular reflector, then the angle of transmission $\theta_t$ is the same as the angle of incidence $\theta_i$, obtained as described in the foregoing. In some examples the relationship between these variables is given by:

$$\Gamma_n = \frac{\sqrt{\varepsilon_{skin}}\cos(\theta_i) - \sqrt{\varepsilon_{air}}\cos(\theta_t)}{\sqrt{\varepsilon_{skin}}\cos(\theta_i) + \sqrt{\varepsilon_{air}}\cos(\theta_t)}, \Gamma_P = \frac{\sqrt{\varepsilon_{air}}\cos(\theta_i) - \sqrt{\varepsilon_{skin}}\cos(\theta_t)}{\sqrt{\varepsilon_{air}}\cos(\theta_i) + \sqrt{\varepsilon_{skin}}\cos(\theta_t)}.$$

The dielectric properties 308 of the target user's skin can be obtained from the calculated value of the permittivity of skin $\varepsilon_{skin}$.

The target user 103 is the person towards whom the electromagnetic radiation 111 is transmitted. The target user 103 may or may not be the user of the apparatus 201. For example, the user of the apparatus 201 may cause the transmitted electromagnetic radiation 111 to be directed towards themselves, making themselves the target user 103, or may cause the transmitted electromagnetic radiation 111 to be directed towards another person, making that other person the target user 103.

The method 301 may comprise prioritizing obtaining skin dielectric properties 308 at certain locations on the target user's body. The plurality of locations 113 towards which the electromagnetic radiation 111 is transmitted may correspond to these certain prioritized locations. The plurality of locations 113 towards which the electromagnetic radiation 111 is transmitted can comprise expected locations of the at least two devices 105 on the target user's body.

The expected locations can comprise locations where WBAN devices are usually found such as, for example, the ears, wrists, and upper thigh/hips. The expected locations may be based on knowledge of the type of devices in the WBAN. For example, hearables will be expected to be located at an ear of the target user 103, smartwatches will be expected to be located at a wrist of the target user 103, and smartphones may be expected to be located around the target user's hip, in a pocket. Alternatively, the expected locations of the at least two devices 105 may correspond to locations on the body of the user 101 at which the at least two devices 105 were reported to be at the time when they were exchanging the wireless signals 107 from which the propagation profile 304 is obtained.

The plurality of locations 113 towards which the electromagnetic radiation 111 is transmitted can comprise locations along an approximate geodesic path between the expected locations of the at least two devices 105. Creeping waves, by means of which the wireless signals 107 between devices 105 propagate, are expected to at least approximately follow geodesic paths between the devices 105. Accordingly, by obtaining dielectric properties 308 of the target user's skin along the approximate geodesic path between the expected locations of the at least two devices 105, it is possible to assess with improved confidence whether an obtained propagation profile 304 correlates with a creeping wave which is realizable on the body of the target user 103.

Multiple paths may be taken by creeping waves between devices 105 on opposite sides of the target user's body. One path may be followed around the rear surface of the target user's body, and another path may be followed around the front surface of the target user's body. Each of these may be geodesic paths in respective directions of travel. Creeping waves may be expected to at least approximately follow geodesic paths in opposite directions of travel and dielectric properties 308 of the target user's skin can be obtained at locations along these paths. In some examples, however, the design of the wireless transceivers in the devices 105 can mitigate against transmitting wireless signals 107 over multiple paths.

Geodesic paths vary with a body's pose. Dielectric properties 308 of the target user's skin may be obtained for locations 113 which lie along geodesic paths between the expected locations of the at least two devise 105 and in multiple common poses. Common poses can include, for example, those of sitting, standing, and walking.

The transmission of the electromagnetic radiation 111 towards the plurality of locations 113 on the target user's body in block 305 can be caused in response to a trigger event. The trigger event may be, for example, a user input to the apparatus 201, a predefined routine, or a request from one or more applications run on the apparatus 201. The predefined routine may involve periodically or continuously causing transmission of the electromagnetic radiation 111 towards the plurality of locations 113 on the target user's body. The request from the one or more applications may be made when authentication of the target user 103 is required in respect of access to the one or more applications.

In some examples the propagation profile 304 for wireless signals 107 between the devices 105 can be obtained contemporaneously with the dielectric properties 308 of the target user's skin based on reflections of the electromagnetic radiation 111. The trigger event may cause the contemporaneous performance of blocks 303 and 305 of the method 301.

Where the frequency of the wireless signals 107 is varied so as to enable propagation profiles 304 to be obtained for different depths of the skin, the electromagnetic radiation 111 transmitted towards the plurality of locations 113 may also be correspondingly varied. This enables dielectric properties 308 at different depths of the skin to be obtained at the plurality of locations 113.

Block 309 of the method 301 comprises determining whether the propagation profile 304 for wireless signals 107 between the at least two devices 105 correlates with a realizable creeping wave along the target user's skin. A realizable creeping wave is a creeping wave that can be realized on the body of the target user 103 given the dielectric properties 308 of their skin. Hence, the realizability of said creeping waves is based on the dielectric properties 308 of their skin obtained according to block 307 of the method 301.

Example implementations of block 309 of the method 301 are shown in FIGS. 4 and 5.

In the example of FIG. 4, determining whether the obtained propagation profile 304 for wireless signals 107 between the at least two devices 105 correlates with a realizable creeping wave along the target user's skin comprises, at block 401, predicting one or more propagation profiles 402 for one or more realizable creeping waves along the target user's skin.

The realizability of a creeping wave along the target user's skin is based on the obtained dielectric properties 308 of the target user's skin. Accordingly, the one or more predicted propagation profiles 402 are based on the obtained dielectric properties 308 of the target user's skin.

Multiple different creeping waves may be realizable since there are multiple paths that creeping waves can take over the target user's skin. Propagation profiles 402 may be predicted for these multiple realizable creeping waves.

Creeping waves at least approximately follow geodesic paths between the at least two devices 105. Geodesic paths vary with a body's pose. For example, the geodesic path between a wrist and an ear while the arm is pinned to the flank is via the chest whereas it is via the shoulder when the arm is outstretched.

If the pose at the time when the at least two devices 105 were exchanging the wireless signals 107 from which the propagation profile 304 is obtained is known, then the number of realizable creeping waves for which propagation profiles 402 may be predicted can be reduced. Likewise, if the locations of the at least two devices 105 at the time when the at least two devices 105 were exchanging the wireless signals 107 from which the propagation profile 304 is obtained are known, then the number of realizable creeping waves for which propagation profiles 402 may be predicted can be reduced. Where one or both of the pose and locations of the at least two devices 105 are unknown for the time when the devices 105 were exchanging the wireless signals 107 from which the propagation profile 304 is obtained, more propagation profiles 402 may be predicted.

In some examples multiple propagation profiles 402 are predicted using the obtained dielectric properties 308 of the target user's skin at locations along different geodesic paths between different pairs of locations where it is expected that WBAN devices may be located and in different common poses. Common poses can include, for example, those of sitting, standing, and walking.

In some examples multiple propagation profiles 402 are predicted using the obtained dielectric properties 308 of the target user's skin at locations along different geodesic paths between locations where the at least two devices 105 may be expected, given the type of device they are, and in different common poses.

In some examples multiple propagation profiles 402 are predicted using the obtained dielectric properties 308 of the target user's skin at locations along different geodesic paths between locations corresponding to those at which the at least two devices 105 are reported to be when exchanging the wireless signals 107 from which the propagation profile 304 is obtained and in different common poses.

In some examples multiple propagation profiles 402 are predicted using the obtained dielectric properties 308 of the target user's skin at locations along different geodesic paths between different pairs of locations where it is expected that WBAN devices may be located and in a pose that was reported at the time when the at least two devices 105 were exchanging the wireless signals 107 from which the propagation profile 304 is obtained.

In some examples one or more propagation profiles 402 are predicted using the obtained dielectric properties 308 of the target user's skin at locations along one or more geodesic paths between locations where the at least two devices 105 may be expected, given the type of device they are, and in a pose that was reported at the time when the at least two devices 105 were exchanging the wireless signals 107 from which the propagation profile 304 is obtained.

In some examples a propagation profile 402 is predicted using the obtained dielectric properties 308 of the target user's skin at locations along a geodesic path between locations corresponding to those at which the at least two devices 105 are reported to be when exchanging the wireless signals 107 from which the propagation profile 304 is obtained and in a pose that was reported at the time when the at least two devices 105 were exchanging the wireless signals 107 from which the propagation profile 304 is obtained.

At block 403, the one or more predicted propagation profiles 402 are then compared with the obtained propagation profile 304 to determine whether any of these predicted propagation profiles 402 correlate with the obtained propagation profile 304 for wireless signals 107 between the at least two devices 105.

In the example of FIG. 5, determining whether the obtained propagation profile 304 for wireless signals 107 between the at least two devices 105 correlates with a realizable creeping wave along the target user's skin comprises, at block 501, predicting dielectric properties 502 of the skin of the user 101 of the at least two devices 105.

Since the realizability of a creeping wave along the target user's skin is based on the dielectric property values 308 of their skin, correlation between the obtained propagation profile 304 and a realizable creeping wave along the target user's skin can be assessed by predicting dielectric properties 502 based on the obtained propagation profile 304 and comparing these with the dielectric properties 308 of the target user's skin.

There are multiple creeping wave paths that the wireless signals 107 may have followed over the body of the user 101 of the at least two devices 105. The paths that would be followed depend on the locations of the at least two devices 105 when they were exchanging the wireless signals 107 and the pose of the user 101 when the at least two devices 105 were exchanging the wireless signals 107.

Where one or both of the locations and the pose are unknown, it is uncertain which path the wireless signals 107 would have followed. Accordingly, dielectric properties 502 can be predicted from the obtained propagation profile 304 in respect of multiple possible paths that the wireless signals 107 could have followed.

The multiple possible paths can include paths between: locations where it is expected that WBAN devices may be located; locations where the at least two devices 105 may be expected, given the type of device they are; and locations corresponding to those at which the at least two devices 105 are reported to be when exchanging the wireless signals 107 from which the propagation profile 304 is obtained. The multiple possible paths can include geodesic paths between the aforementioned locations in multiple common poses or in a pose that was reported at the time when the at least two devices 105 were exchanging the wireless signals 107 from which the propagation profile 304 is obtained. The curvature of the paths is dependent on the body surface topography of the user 103. Body surface topography information may be provided as an input. The format of such an input may be as a sequence of radius of curvatures for points intervening the aforementioned locations.

Where one or both of the locations and the pose are known, the number of paths that the wireless signals 107 could have followed is reduced.

In some examples the predicted dielectric properties 502 may comprise an average along the path rather than localized dielectric properties for different locations along the path.

At block 503, the predicted dielectric properties 502 can be compared to the obtained dielectric properties 308 of the target user's skin to determine whether there is a correlation between the dielectric properties 502 of the skin of the user 101 predicted from the obtained propagation profile 304 and dielectric properties 308 of the skin of the target user 103 which define which creeping waves are realizable.

Machine learning can be used with a training set comprising ground truth dielectric properties 308 of skin and pose information and output variables comprising ground truth propagation profiles 304, gathered during an experimentation and testing phase, to learn a function or algorithm which maps dielectric properties 308 to a propagation profile 304. Alternatively, one or more specified rules may be provided which map dielectric properties 308 to a propagation profile 304.

The pose at the time when the at least two devices 105 were exchanging the wireless signals 107 from which the propagation profile 304 is obtained can be determined using sensors comprised in the at least two devices 105. For example, where the devices 105 comprise means for performing positional tracking such as an accelerometer and gyrometer, in combination providing tracking with 6DoF, then an algorithm can be trained via machine learning to identify poses based on movements characterizing transitions between different poses. In scenarios like walking the pose can be identified from the phase of the walking cycle indicated by rhythmic vibrations. The pose at the time when the at least two devices 105 were exchanging the wireless signals 107 from which the propagation profile 304 is obtained can also be determined using sensors comprised in the apparatus 201 or a device in which the apparatus 201 is also comprised. For example, radar and optical imaging can be used to determine pose.

In some examples, of all the wireless signals exchanged between the at least two devices 107, it is those which are exchanged while the user 101 is identified to be in a common pose from which the propagation profile 304 is obtained. Accordingly, this then reduces the number of realizable creeping waves against which to assess the propagation profile 304 to determine whether or not there is correlation.

Returning FIG. 3, a realizable creeping wave which is determined to correlate with the obtained propagation profile 304 in block 309 can be used to determine the locations of the at least two devices 105 on the target user's body where these locations are not already known. The method 301 can comprise determining, from a path of a realizable creeping wave which correlates with the propagation profile 304 for wireless signals 107 between the at least two devices 105, locations of the at least two devices 105 on the target user's body. Knowledge of the locations of the at least two devices 105 on the target user's body enables an additional check to be performed on incoming wireless signals to confirm whether they are transmitted from one of the at least two devices 105. A directionality of incoming wireless signals can be determined. Based on the directionality of the incoming wireless signals, it can be assessed whether or not they are transmitted from the locations of the at least two devices 105. If the directionality of the incoming wireless signals indicates that they are transmitted from the location of one of the at least two devices 105, it can be determined that the incoming wireless signals are transmitted from one of at least two the devices 105. This can provide an extra layer of security in validating that the incoming wireless signals are from a trusted source.

In some examples, the dielectric properties 308 of the target user's skin can be recorded in the form of an addressable data structure that is retrievable from an addressable memory space (for example, the memory 207) and can therefore be stored and retrieved until deleted or overwritten, although long-term storage may or may not occur. Accordingly, blocks 305 and 307 may not be performed every time that a determination as to whether the propagation profile 304 for wireless signals 107 between the at least two devices 105 correlates with a realizable creeping wave along the target user's skin (block 309) is performed. However, since dielectric properties of skin change over time due to environmental (including seasonal) effects on, for example, skin hydration, there may be a limit to how long after the dielectric properties 308 are recorded they can still be relied upon. In some examples though, by observing the target user over a range of environmental conditions, predictable variations from the recorded dielectric properties 308 can be accounted for when considering the realizability of a creeping wave.

At block 311 of the method 301 an association is formed between the target user 103 and the at least two devices 105 based on a strength of correlation between the propagation profile 304 and a realizable creeping wave.

In some example, while a weak correlation between the propagation profile 304 and a realizable creeping wave may be determined, this can be insufficient to initiate the forming of an association between the target user 103 and the at least two devices 105. For example, where the association is connected to authorization and access control, for the purposes of security the determination of a strong correlation between the propagation profile 304 and a realizable creeping wave may be a condition for forming the association between the target user 103 and the at least two devices 105. It is to be appreciated that the value of a correlation coefficient that indicates a strong correlation is dependent on the particular statistical measure used.

If the target user 103 is an authorized user of the apparatus 201, as may be determined independently by, for example, passcode entry at the apparatus 201, then the formed association between the target user 103 and the at least two devices 105 can cause connection of the apparatus 201 with the at least two devices 105 to be approved. In this case the association implies that the at least two devices 105 are located within, on, or in the immediate proximity of the body of an authorized user suggesting that these at least two devices 105 are owned by or at least in the possession of the authorized user and can accordingly be trusted.

If the at least two devices 105 are approved to connect with the apparatus 201 or already connected with the apparatus 201, then the formed association between the target user 103 and the at least two devices 105 can cause access for the target user 103 to applications run on the apparatus 201 to be approved. In this case the association implies that trusted devices are located within, on, or in the immediate proximity of the body of the target user 103 suggesting that the target user 103 is the owner or at least possessor of the trusted devices and can accordingly be trusted.

Dielectric properties of skin change over time due to environmental (including seasonal) effects on, for example, skin hydration. This makes authorization and access control based on the method 301 more secure, analogous to the effect of periodic password resets.

Where a structural feature has been described, it may be replaced by means for performing one or more of the functions of the structural feature whether that function or those functions are explicitly or implicitly described.

Consequently, in some examples, the apparatus 201 comprises means for: obtaining 303 a propagation profile 304 for wireless signals 107 transmitted between at least two devices 105 via a creeping wave along a user's skin; causing transmission 305 of electromagnetic radiation 111 towards a plurality of locations 113 on a target user's body to obtain 307 dielectric properties 308 of their skin at the plurality of locations 113 based on an amount of the electromagnetic radiation 111 reflected from each location 113; determining 307 whether the propagation profile 304 correlates with a realizable creeping wave along the target user's skin, the realizability being based on the obtained dielectric properties 308 of their skin; and forming 309 an association between the target user 103 and the at least two devices 105 based on a strength of correlation between the propagation profile 304 and a realizable creeping wave.

The analyzing of the wireless signals 107 and the processing of the reflected electromagnetic radiation 111 may involve artificial intelligence or machine learning algorithms. The data may, for example, be used as learning input to train a machine learning network or may be used as a query input to a machine learning network, which provides a response. The machine learning network may for example use linear regression, logistic regression, vector support machines or an acyclic machine learning network such as a single or multi hidden layer neural network.

Machine learning, which can include statistical learning, is a field of computer science that gives computers the ability to learn without being explicitly programmed. The computer learns from experience E with respect to some class of tasks T and performance measure P if its performance at tasks in T, as measured by P, improves with experience E. The computer can often learn from prior training data to make predictions on future data. Machine learning includes wholly or partially supervised learning and wholly or partially unsupervised learning. It may enable discrete outputs (for example classification, clustering) and continuous outputs (for example regression). Machine learning may for example be implemented using different approaches such as cost function minimization, artificial neural networks, support vector machines and Bayesian networks for example. Cost function minimization may, for example, be used in linear and polynomial regression and K-means clustering. Artificial neural networks, for example with one or more hidden layers, model complex relationship between input vectors and output vectors. Support vector machines may be used for supervised learning. A Bayesian network is a directed acyclic graph that represents the conditional independence of a number of random variables.

The above described examples find application as enabling components of:
automotive systems; telecommunication systems; electronic systems including consumer electronic products; distributed computing systems; media systems for generating or rendering media content including audio, visual and audio visual content and mixed, mediated, virtual and/or augmented reality; personal systems including personal health systems or personal fitness systems; navigation systems; user interfaces also known as human machine interfaces; networks including cellular, non-cellular, and optical networks; ad-hoc networks; the internet; the internet of things; virtualized networks; and related software and services.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one" or by using "consisting".

In this description, reference has been made to various examples. The description of features or functions in relation to an example indicates that those features or functions are present in that example. The use of the term "example" or "for example" or "can" or "may" in the text denotes, whether explicitly stated or not, that such features or functions are present in at least the described example, whether described as an example or not, and that they can be, but are not necessarily, present in some of or all other examples. Thus "example", "for example", "can" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although examples have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain examples, those features may also be present in other examples whether described or not.

The term "a" or "the" is used in this document with an inclusive not an exclusive meaning. That is any reference to X comprising a/the Y indicates that X may comprise only one Y or may comprise more than one Y unless the context clearly indicates the contrary. If it is intended to use "a" or "the" with an exclusive meaning then it will be made clear in the context. In some circumstances the use of 'at least one' or 'one or more' may be used to emphasis an inclusive meaning but the absence of these terms should not be taken to infer any exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus comprising:
   at least one processor; and
   at least one memory including computer program code, the at least one memory and the computer program code configured to, with the at least one processor, cause the apparatus at least to:
   obtain a propagation profile for wireless signals transmitted between at least two devices via a creeping wave along a user's skin;
   cause transmission of electromagnetic radiation towards a plurality of locations on a target user's body to obtain dielectric properties of the target user's skin at the plurality of locations based on an amount of the electromagnetic radiation reflected from each location;
   determine whether the propagation profile correlates with a realizable creeping wave along the target user's skin, the realizability being based on the obtained dielectric properties of the target user's skin; and
   form an association between the target user and the at least two devices based on a strength of correlation between the propagation profile and a realizable creeping wave.

2. The apparatus of claim 1 wherein the propagation profile indicates attenuation of one or more frequencies of the wireless signals.

3. The apparatus of claim 1 wherein the at least one memory and the computer program code are configured to, with the at least one processor, further cause the apparatus to: receive the propagation profile from at least one of one of the at least two devices.

4. The apparatus of claim 1 wherein the apparatus is or is comprised in one of the at least two devices and obtains the propagation profile by analysis of wireless signals received from another of the at least two devices.

5. The apparatus of claim 1 wherein the at least two devices are Wireless Body Area Network (WBAN) devices.

6. The apparatus of claim 1 wherein the electromagnetic radiation transmitted towards the plurality of locations comprises at least one radiofrequency beam having a wavelength below 10 mm.

7. The apparatus of claim 1 wherein the plurality of locations towards which the electromagnetic radiation is transmitted comprise expected locations on the target user's body of the at least two devices.

8. The apparatus of claim 1 wherein the dielectric properties of the target user's skin at the plurality of locations are obtained based on the amount of the electromagnetic radiation reflected back to the apparatus.

9. The apparatus of claim 1 wherein the at least one memory and the computer program code are configured to, with the at least one processor, further cause the apparatus to: predict propagation profiles for realizable creeping waves based on obtained dielectric properties of the target user's skin.

10. The apparatus of claim 1 wherein the propagation profiles are predicted for realizable creeping waves between expected locations on the target user's body of the at least two devices.

11. The apparatus of claim 1 wherein the at least one memory and the computer program code are configured to, with the at least one processor, further cause the apparatus to: predict dielectric properties of the target user's skin based on the obtained propagation profile.

12. The apparatus of claim 1 wherein the at least one memory and the computer program code are configured to, with the at least one processor, further cause the apparatus to: in response to an association between the target user and the at least two devices being made, and in response to the target user being an authorized user of the apparatus, approve connection of the apparatus with the at least two devices.

13. The apparatus of claim 1 wherein the at least one memory and the computer program code are configured to, with the at least one processor, further cause the apparatus to: in response to an association between the target user and at least two devices being made, and in response to the target user being approved to connect the with the apparatus, approve access for the target user to applications run on the apparatus.

14. A method comprising:
   obtaining a propagation profile for wireless signals transmitted between at least two devices via a creeping wave along a user's skin;
   causing transmission of electromagnetic radiation towards a plurality of locations on a target user's body to obtain dielectric properties of the target user's skin at the plurality of locations based on an amount of the electromagnetic radiation reflected from each location;
   determining whether the propagation profile correlates with a realizable creeping wave along the target user's skin, the realizability being based on the obtained dielectric properties of the target user's skin; and
   forming an association between the target user and the at least two devices based on a strength of correlation between the propagation profile and a realizable creeping wave.

15. The method of claim 14, further comprising receiving the propagation profile from at least one of the at least two devices.

16. The method of claim 14, wherein the at least two devices are Wireless Body Area Network (WBAN) devices.

17. The method of claim 14, wherein the electromagnetic radiation transmitted towards the plurality of locations comprises at least one radiofrequency beam having a wavelength below 10 mm.

18. A non-transitory computer readable medium comprising program instructions stored thereon for performing at least the following:
   obtaining a propagation profile for wireless signals transmitted between at least two devices via a creeping wave along a user's skin;
   causing transmission of electromagnetic radiation towards a plurality of locations on a target user's body to obtain dielectric properties of the target user's skin at the plurality of locations based on an amount of the electromagnetic radiation reflected from each location;
   determining whether the propagation profile correlates with a realizable creeping wave along the target user's skin, the realizability being based on the obtained dielectric properties of the target user's skin; and
   forming an association between the target user and the at least two devices based on a strength of correlation between the propagation profile and a realizable creeping wave.

19. The non-transitory computer readable medium of claim 18, wherein the program instructions are further configured to cause: receiving the propagation profile from at least one of the at least two devices.

20. The non-transitory computer readable medium of claim 18, wherein the electromagnetic radiation transmitted towards the plurality of locations comprises at least one radiofrequency beam having a wavelength below 10 mm.

* * * * *